United States Patent
Egle et al.

(10) Patent No.: US 8,722,412 B2
(45) Date of Patent: May 13, 2014

(54) IDENTIFICATION SYSTEM FOR SPECIMEN SLIDES

(75) Inventors: Markus Egle, Sinsheim (DE); Stefan Thiem, Heidelberg (DE); Simon Keimer, Nussloch (DE); Karl-Heinz Westerhoff, Eppingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 148 days.

(21) Appl. No.: 13/338,289

(22) Filed: Dec. 28, 2011

(65) Prior Publication Data
US 2012/0171003 A1 Jul. 5, 2012

(30) Foreign Application Priority Data
Dec. 29, 2010 (DE) .......................... 10 2010 061 611

(51) Int. Cl.
*G01N 35/00* (2006.01)
*G01N 1/31* (2006.01)

(52) U.S. Cl.
CPC .......... *G01N 35/00732* (2013.01); *G01N 1/312* (2013.01); *G01N 35/0099* (2013.01); *G01N 2035/00039* (2013.01); *G01N 2035/00138* (2013.01)
USPC ................................ 436/46; 422/536; 422/65

(58) Field of Classification Search
None
See application file for complete search history.

(56) References Cited

U.S. PATENT DOCUMENTS

| | | | |
|---|---|---|---|
| 2004/0009098 A1* | 1/2004 | Torre-Bueno | 422/63 |
| 2006/0039822 A1* | 2/2006 | Domack | 422/63 |
| 2007/0148046 A1 | 6/2007 | Nakaya | |
| 2008/0013185 A1 | 1/2008 | Garoutte et al. | |

FOREIGN PATENT DOCUMENTS

| | | |
|---|---|---|
| DE | 10 2005 021 197 | 7/2006 |
| DE | 10 2005 012 745 | 8/2006 |
| DE | 10 2007 042 138 | 5/2007 |
| EP | 1804046 A2 | 4/2007 |
| GB | 2441594 A | 12/2008 |
| JP | 57-199958 * | 12/1982 |
| WO | 02075425 A1 | 9/2002 |

* cited by examiner

*Primary Examiner* — P. Kathryn Wright
(74) *Attorney, Agent, or Firm* — Hodgson Russ LLP

(57) ABSTRACT

An apparatus for sensing specimen slides (38) has a specimen slide holder (42) holding specimen slides (38), each specimen slide (38) comprising an identification code. The specimen slides (38) are arranged inside the specimen slide holder (42) on a lifting element (50) in a lifted position. The apparatus includes a reading apparatus (40) for reading out the identification code, and a positioning apparatus that moves the specimen slide holder (42) with the specimen slides (38) relative to the lifting element (50) so that the specimen slides (38) drop successively from the lifted position on the lifting element (50). As one of the specimen slides (38) drops, the identification code of the specimen slide (38) or of the subsequent specimen slide (38) becomes readable for the reading apparatus (40). A triggering apparatus (67, 68) triggers the reading apparatus (40) to read the identification code.

10 Claims, 6 Drawing Sheets

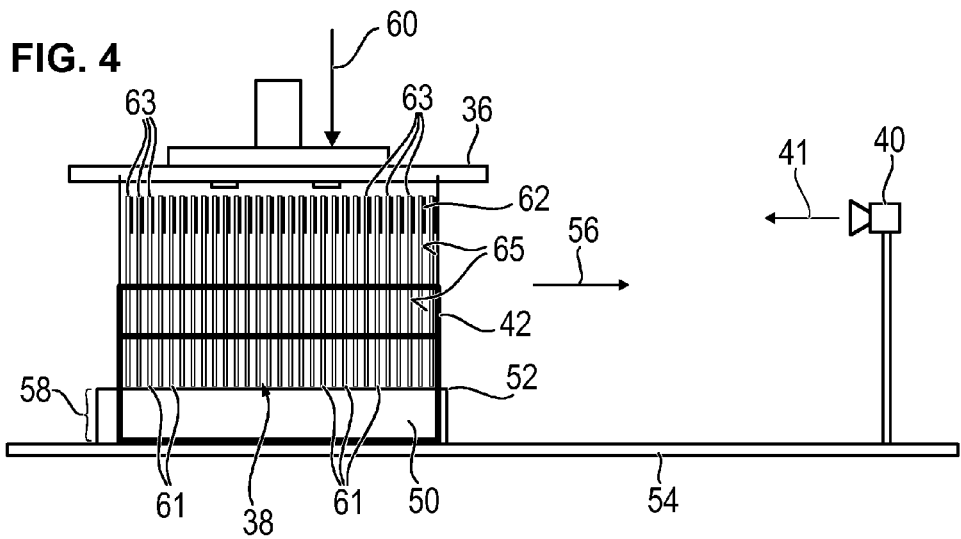
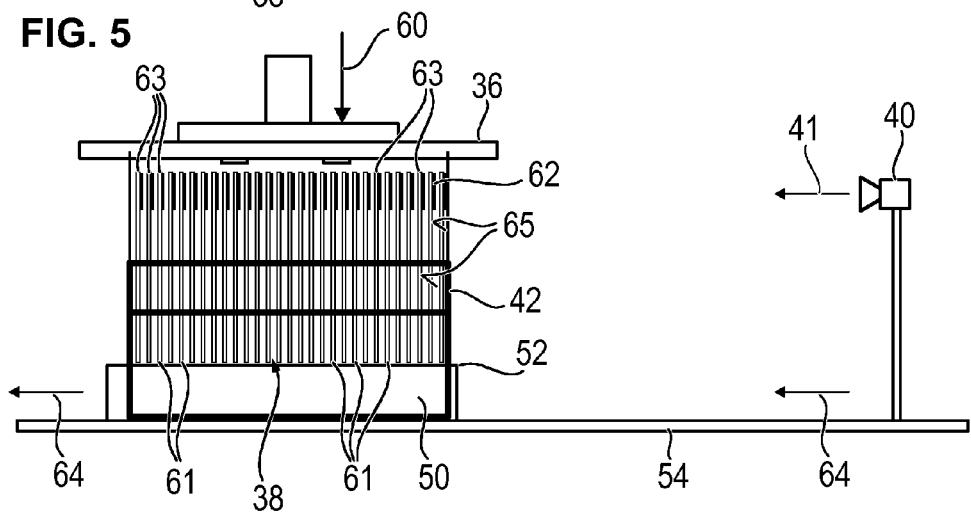
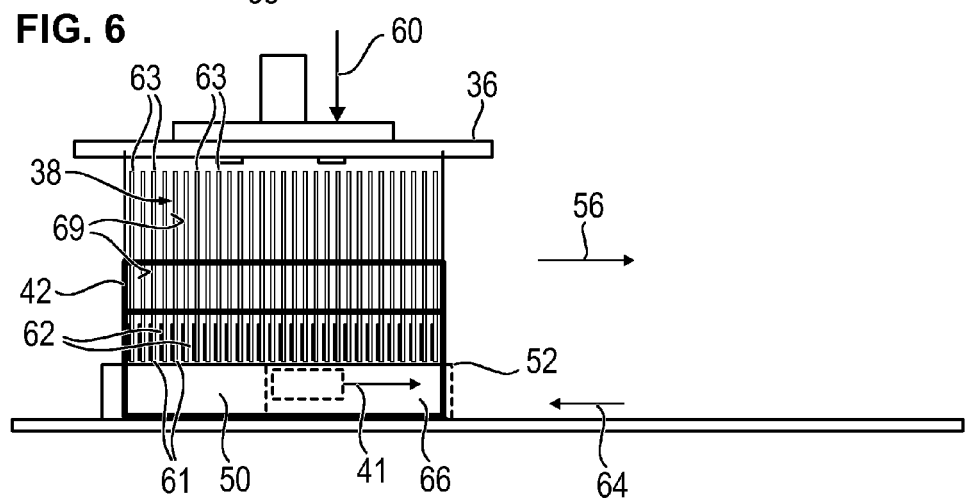

IDENTIFICATION SYSTEM FOR SPECIMEN SLIDES

CROSS REFERENCE TO RELATED APPLICATIONS

This application claims priority of German patent application number 10 2010 061 611.7 filed Dec. 29, 2010, the entire disclosure of which is incorporated by reference herein.

FIELD OF THE INVENTION

The present invention relates generally to an apparatus and a method for sensing specimen slides.

BACKGROUND OF THE INVENTION

For the investigation of samples, for example tissue samples, the latter are prepared and are mounted onto a specimen slide. The samples on the specimen slides can then be automatically coverslipped with the aid of a coverslipper, and/or automatically stained with the aid of a stainer. The samples are coverslipped or stained so that they can subsequently be investigated with the aid of a microscope.

It is known to equip the specimen slides with identification codes, for example barcodes, allowing the specimen slides, and in particular the specimens on the specimen slides, to be automatically identified, so that processing in the coverslipper or stainer can occur automatically.

DE 10 2007 042 138 A1 describes a device and a method for automatic sample delivery, the samples being held on a specimen slide that is arranged in a specimen slide box. Each sample is characterized by a barcode that is automatically read out for identification of the sample.

DE 10 2005 021 197 B3 and 10 2005 012 745 B3 describe an apparatus for handling and allocating microtomed tissue samples. The tissue samples are arranged on specimen slides that are equipped with a machine-readable code. Upon handling of the specimen slides, the code is read out with the aid of a reading unit.

US 2008/0137185 A1 and US 2007/0148046 A1 describe devices for handling specimen slides for tissue samples. Each specimen slide carries a code for identifying the tissue sample that is held.

SUMMARY OF THE INVENTION

It is an object of the present invention to create a method and an apparatus for sensing specimen slides that enable, in a particularly simple and reliable manner, identification of the specimen slides and in particular of the samples on the specimen slides.

This object is achieved by a method and an apparatus having the features described herein. Advantageous embodiments are described in the present specification.

According to a first aspect, the invention is notable for a lifting element on which the specimen slides are arranged inside the specimen slide holder in a lifted position. A positioning apparatus moves the specimen slide holder with the specimen slides relative to the lifting element so that the specimen slides drop successively from the lifted position on the lifting element into a final position in the specimen slide holder. The identification codes are arranged on the specimen slides in such a way that as one of the specimen slides drops, the identification code of the corresponding specimen slide or of the subsequent specimen slide becomes readable for the reading apparatus. As soon as the identification code of the corresponding specimen slide is readable, the reading apparatus reads out the identification code in reaction to a signal of a triggering apparatus.

A sample is arranged on each of the specimen slides, and the identification code serves in particular to identify the sample on the specimen slide. The specimen slides are preferably arranged with their sample-carrying surface oriented parallel to a vertical line, so that an upper edge and a lower edge are clearly defined. The lifting element preferably has a horizontal upper side on which the lower edges of the specimen slides stand. The lifting element lifts the specimen slides only sufficiently far that the latter are still located at least partly in the specimen slide holder, and are moved with it. The lifting element has a defined length, preferably in a horizontal direction, the motion amplitude of the specimen slide holder as a result of the motion of the positioning apparatus being greater than the length of the lifting element, with the result that upon movement of the specimen slide holder by way of the lifting element, preferably in a horizontal direction, the specimen slides at the end of the lifting element drop into the final position in the specimen slide holder. The relative motion between the lifting element and the specimen slide holder can be implemented by a motion of the specimen slide holder, or by a motion of the lifting element, or by an oppositely directed motion of the lifting element and the specimen slide holder.

The identification codes are preferably arranged close to the upper edge or close to the lower edge of the specimen slides in the specimen slide holder, so that as one of the specimen slides drops, it exposes for readout either the identification code, arranged close to the upper edge, of the subsequent specimen slide, or its own identification code arranged close to the lower edge. The upper and the lower edge of the specimen slide are defined not by the specimen slides themselves, but by their orientation in the specimen slide holder. The lower edge can also be referred to as a "first edge," and the upper edge also as a "second edge." The specimen slide that is the next to drop after a specimen slide that has dropped is referred to as a "subsequent specimen slide."

Exposing the identification code with the aid of the lifting element and in particular by employing gravity, and the automatic reading of the identification code thereby triggered, represent a particularly simple capability for identifying the specimen slides within the specimen slide holder. In particular, particularly few mechanical and electronic components are needed, with the result that malfunction susceptibility is minimized and the entire apparatus can be manufactured easily and economically, and maintenance intervals can be extended.

According to an embodiment, a gripper arm that moves the specimen slide holder with the specimen slides onto the lifting element, in such a way that the lifting element lifts the specimen slides in the specimen slide holder into the lifted position, is arranged. The gripper arm can, for example, slide the specimen slide holder onto the lifting element or place it onto the lifting element. As an alternative thereto, the lifting element can also be slid under the specimen slide holder and/or introduced from below into the specimen slide holder, and can lift the specimen slides in the specimen slide holder into the lifted position. This makes it possible to lift the specimen slides inside the specimen slide holder in particularly simple fashion.

In an advantageous embodiment, the lifting element comprises an edge at which the specimen slides drop from the lifted position on the lifting element into their final position in the specimen slide holder. The edge thus characterizes the end of the lifting element. A spacing between the edge and the reading apparatus is preferably constant. This contributes to the ability of the reading apparatus to reliably read out the identification code. A camera can be provided, in particular, as a reading apparatus, and the edge can be arranged so that the identification codes are always located in the focal plane of a lens of the camera.

The lifting element can encompass a rail or a blade, and the triggering apparatus can encompass a photoelectric barrier. The apparatus for sensing the specimen slides can be an element of a staining apparatus or of a coverslipping apparatus.

According to a second aspect, the invention is notable for a method for sensing specimen slides, the specimen slides being arranged in the specimen slide holder. The specimen slides in the specimen slide holder are arranged in a lifted position with the aid of a lifting element, each of the specimen slides comprising the identification code for identifying the specimen slide. The specimen slide holder with the specimen slides is moved relative to the lifting element so that the specimen slides drop successively from the lifted position into the final position. As one of the specimen slides drops, the identification code of the specimen slide or of the subsequent specimen slide becomes readable for the reading apparatus. The reading apparatus is triggered shortly before or while dropping occurs.

According to a refinement, the specimen slide holder with the specimen slides is moved onto the lifting element so that the lifting element lifts the specimen slides in the specimen slide holder into the lifted position. As an alternative to this, the lifting element can be moved under the specimen slide holder so that once again the lifting element lifts the specimen slides in the specimen slide holder into the lifted position. In addition, the refinements of the apparatus can also be transferred to refinements of the method.

BRIEF DESCRIPTION OF THE DRAWINGS

Exemplifying embodiments of the invention are further explained in more detail below with reference to schematic drawings, in which:

FIG. 4 shows a functional principle of a first exemplifying embodiment of the apparatus for sensing the specimen slides;

FIG. 5 shows a functional principle of a second exemplifying embodiment of the apparatus for sensing the specimen slides;

FIG. 6 shows a functional principle of a third exemplifying embodiment of the apparatus for sensing the specimen slides;

Elements of identical design or function are characterized with the same reference characters throughout the Figures.

DETAILED DESCRIPTION OF THE INVENTION

Figure 1:
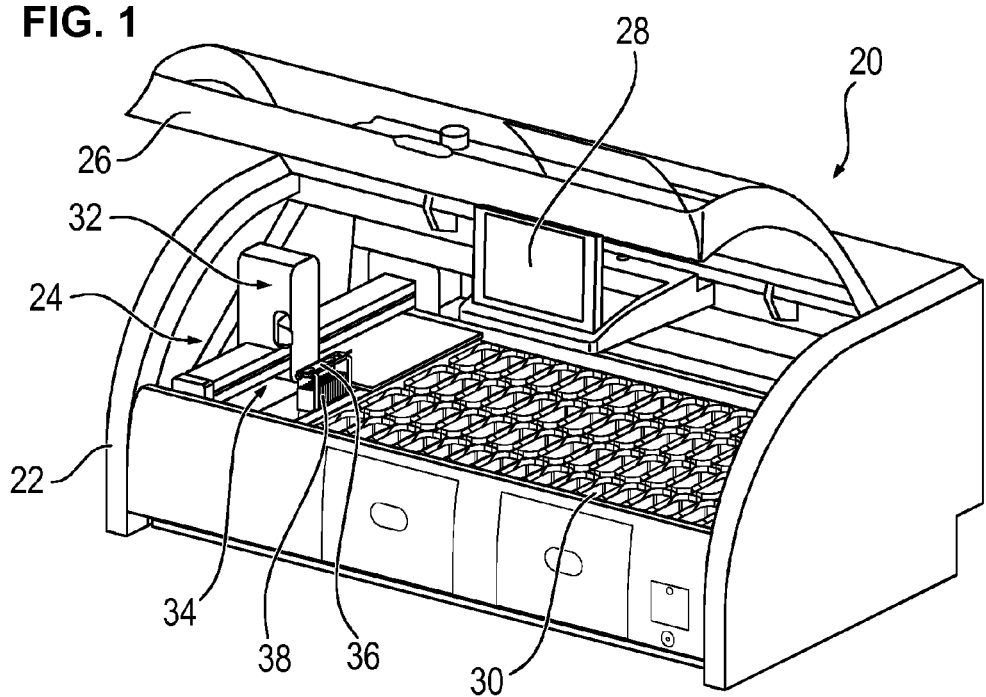
FIG. 1 shows a stainer.

FIG. 1 shows a stainer 20 for staining specimens, in particular samples, in particular tissue samples. Stainer 20 comprises a housing 22 that encloses an interior space 24 that can be covered with the aid of a cover 26. Arranged inside stainer 20 is a monitor 28 on which an operator of stainer 20 can, inter alia, assess a current processing state. Multiple reagent containers 30, in which different reagents for clearing and/or staining the samples are contained, are arranged in interior space 24. The samples are arranged on specimen slides 38 that can be brought, with the aid of a gripper arm 32 and a carrier bracket 36, into the individual reagent containers 30 or to an oven module 34. Oven module 34 is suitable for drying the samples on specimen slides 38 before or after staining of the samples.

Figure 2:
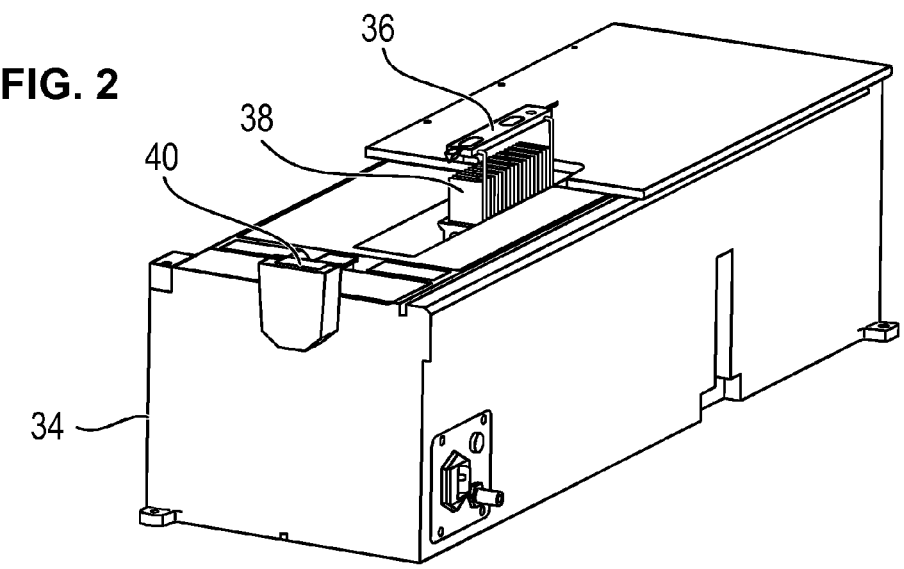
FIG. 2 shows an oven module of the stainer.

FIG. 2 is an enlarged view of oven module 34 with specimen slides 38 and carrier bracket 36. Oven module 34 comprises a reading apparatus 40, in particular a camera. Camera 40 is suitable for reading out an identification code that is arranged on each of specimen slides 38. The identification codes can encompass, for example, barcodes or ordinarily readable written characters. As an alternative thereto, other suitable identification codes and/or a corresponding alternative reading apparatus can be provided; it is necessary only to ensure that the identification codes are readable with the aid of reading apparatus 40. The identification codes are representative of the samples on specimen slides 38 and/or representative of the treatment of the samples that is entailed by the identification. In other words, on the basis of the identification it is possible to determine which treatment process the corresponding sample must subsequently be subjected to, or which treatment process must be omitted. In addition to the identification, the sample can also furthermore be entirely or partly exposed for reading, so that camera 40 can entirely or partly sense the sample. Optical sensing of the sample, and a comparison with a sample block from which the sample was cut, can contribute to recognition as to whether the orientation of specimen slide 38 in specimen slide holder 42 is correct. If it is not correct, the corresponding specimen slide 38 can be removed, for example automatically, and reinserted in correctly oriented fashion. If this correction did not occur, a coverslip would then, after staining of the samples, be attached with the aid of a coverslipper onto the wrong side of specimen slide 38, and the sample would not be suitably covered.

Figure 3:
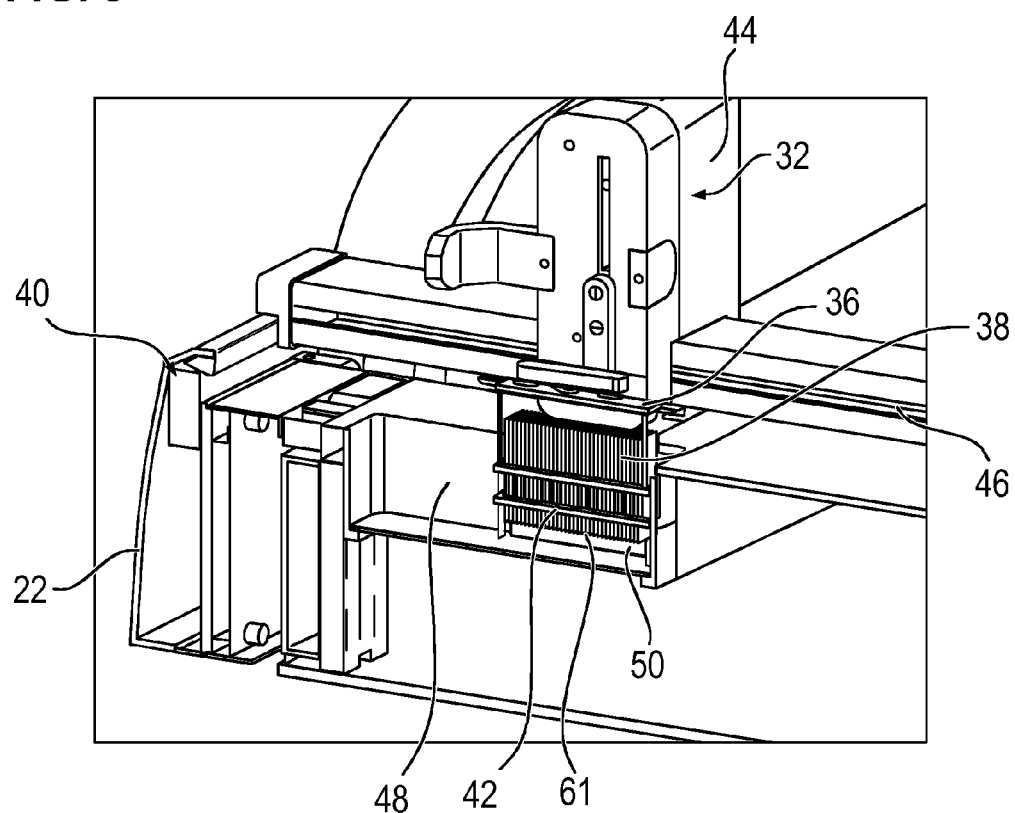
FIG. 3 is a section through the stainer and the oven module.

FIG. 3 shows a section through oven module 34 in stainer 20. Specimen slides 38 are arranged in a specimen slide holder 42 that can also be referred to as a "magazine." Specimen slide holder 42 is located in an identification space 48 in which the identification codes, and thus specimen slides 38 and in particular the samples on specimen slides 38, are sensed. Gripper arm 32 comprises a drive unit 44 and a horizontal guide 46 that enables horizontal and vertical movement of specimen slide holder 42 with specimen slides 38. A lifting element 50 is introduced into specimen slide holder 42 in such a way that specimen slides 38 inside specimen slide holder 42 are arranged in a lifted position, the vertically oriented specimen slides 38 standing upright on their lower edges 61 on lifting element 50. Lower edges 61 can also be referred to as "first edges" 61. Lifting element 50 can encompass, for example a blade or a rail that has, for example, a length corresponding to the length of specimen slide holder 42.

FIG. 4 shows a functional principle of a first exemplifying embodiment of an apparatus for sensing specimen slides 38, and in particular for sensing the identification codes of specimen slides 38 that are associated with the samples on specimen slides 38. The apparatus for sensing specimen slides 38 is thus suitable for sensing the samples on specimen slides 38. The apparatus encompasses specimen slide holder 42, lifting element 50, reading apparatus 40, and a triggering apparatus 67, 68 explained with reference to FIG. 7. Lifting element 50 comprises an edge 52 at its elongated end. Lifting element 50 is fixedly coupled via a coupling element 54 to reading apparatus 40, so that a spacing between edge 52 and reading apparatus 40 is constant. Coupling element 54 can be part of a wall of identification space 48.

Reading apparatus 40 is oriented in a receiving direction 41 in which reading apparatus 40 can sense the identification codes. The identification codes are located on labeling fields 62 that are arranged on specimen slides 38 on surfaces 65 that carry the samples, close to upper edges 63, facing away from lower edges 61, of specimen slides 38. Specimen slides 38 are slid in a vertical direction into specimen slide holder 42 and stand upright on their lower side, in particular their lower edges 61, on lifting element 50. Lifting element 50 has a height 58 by which specimen slides 38 are lifted within specimen slide holder 42 and are thus in a lifted position. Height 58 is, for example, 20 mm. As a result of a lowering of specimen slide holder 42 in lowering direction 60, specimen slides 38 are placed onto lifting element 50 and lifted relative to specimen slide holder 42.

When specimen slide holder 42 is then moved with the aid of a positioning apparatus (not depicted) in a first motion direction 56 toward reading apparatus 40, specimen slides 38 then drop successively, at edge 52, off lifting element 50 into a final position in specimen slide holder 42, which position is delimited by the lower side of specimen slide holder 42. As soon as one of specimen slides 38 drops off lifting element 50, it exposes labeling field 62 and thus the identification code of the subsequent specimen slide 38, which can then be sensed with the aid of reading apparatus 40. Once all the specimen slides 38 of specimen slide holder 42 have been sensed, specimen slide holder 42 is removed from identification space 48 and delivered to the staining process, which preferably occurs as a function of the sensed samples.

FIG. 5 shows a functional principle of a second exemplifying embodiment of the apparatus for sensing specimen slides 38, the components of which apparatus correspond to the first exemplifying embodiment. In contrast to the first exemplifying embodiment shown in FIG. 4, however, it is not specimen slide holder 42 but instead lifting element 50 that is moved, specifically in a second motion direction 64 that is opposite to first motion direction 56. Coupling element 54 couples lifting element 50 to camera 40 so that the spacing between the identification code to be read and the camera is constant; in this exemplifying embodiment, coupling element 54 is not part of the wall of identification space 48. The horizontal motion of lifting element 50 causes specimen slides 38 to drop successively, at the co-moving edge 52, from the elevation position on lifting element 50 into their final position in specimen slide holder 42. The identification codes of the respectively subsequent specimen slides are thereby exposed for reading.

FIG. 6 is a schematic sketch of a third exemplifying embodiment of the apparatus for sensing specimen slides 38, in which example reading apparatus 40 is arranged inside a camera space 66 in lifting element 50. In this exemplifying embodiment, receiving direction 41 is opposite to receiving direction 41 of the previous exemplifying embodiment. The labeling fields are accordingly located not on surfaces 65 of specimen slides 38 close to upper edges 63 of the vertically inserted specimen slides 38, but instead on rear sides 69, facing away from surfaces 65, of specimen slides 38 close to the their lower edges 61. The result of this is that, as specimen slides 38 drop, the respective labeling field 62 of specimen slide 38 that has just dropped becomes readable for reading apparatus 40, so that the latter can read out the identification code. Upper edges 63 and lower edges 61 are defined not by specimen slides 38 themselves, but instead by their vertical orientations inside specimen slide holder 42. In contrast to the motion of specimen slide holder 42, lifting element 50 can also be moved, corresponding to the difference between the exemplifying embodiments shown in FIGS. 4 and 5. In addition, in all the exemplifying embodiments the samples can also be arranged on rear sides 69.

Figure 7:
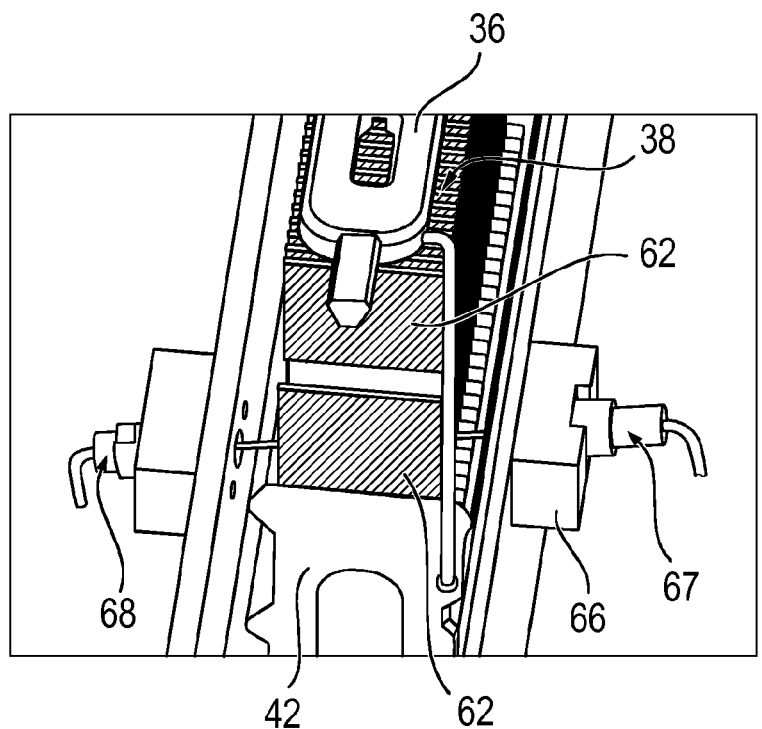
FIG. 7 shows a triggering apparatus.

FIG. 7 shows the triggering apparatus, which encompasses a transmitter 67 and a receiver 68. Transmitter 67 and receiver 68 are, for example, constituted respectively by a light source and a light sensor that together form a photoelectric barrier. Triggering apparatus 67, 68 is arranged so that it triggers reading apparatus 40, at the correct time before or while specimen slide 38 drops into the final position, to read the identification code. Triggering apparatus 67, 68 can, for example, trigger reading apparatus 40 shortly before or upon the impact of specimen slide 38. As an alternative thereto, triggering apparatus 67, 68 can already be triggered by specimen slide 38 while the latter is still located on lifting element 50, in which case reading apparatus 40 is then triggered with a time delay that is linked to a movement velocity of the positioning apparatus for moving specimen slide holder 42 or lifting element 50, so that reading apparatus 40 is triggered as long as the identification code is readable. Preferably at least a first and a last triggering signal of triggering apparatus 67, 68 are discarded, since holding elements of specimen slide holder 42 can also pass through triggering apparatus 67, 68 and are not intended thereby to trigger a reading operation.

Figure 8:
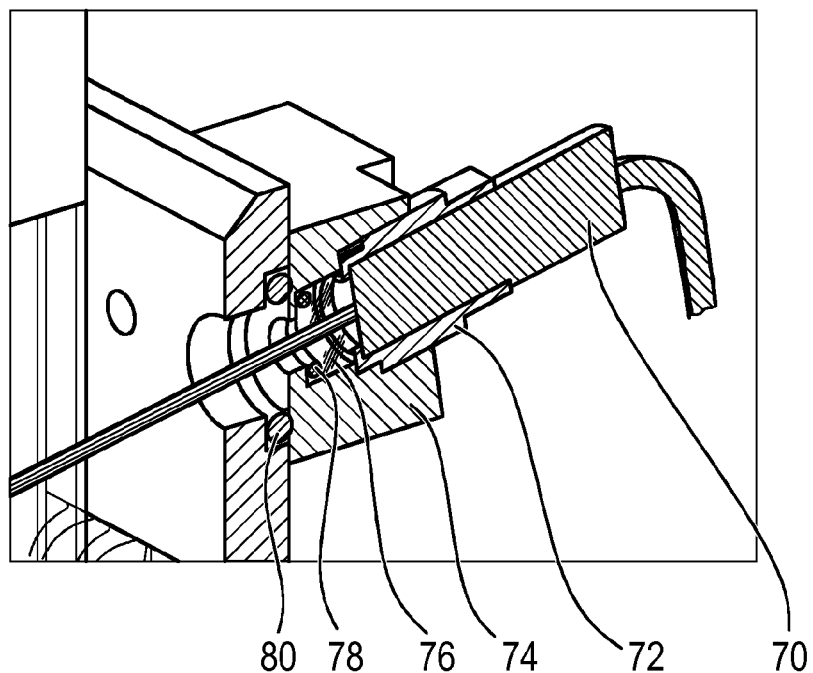
FIG. 8 shows a reading apparatus.

FIG. 8 is a detail view of camera 40. Camera 40 encompasses a sensor 70, in particularly a light-sensitive sensor, that is arranged in a sleeve 72. Sleeve 72 is mounted on a bearing 74, and is delimited by a glass window 76. Sensor 70 behind glass window 76 is sealed off with respect to an interior space of oven module 34 with the aid of a first sealing ring 78 and a second sealing ring 80. Glass window 76 can contribute to suppressing penetration of reagent vapors toward sensor 70.

Figure 9:
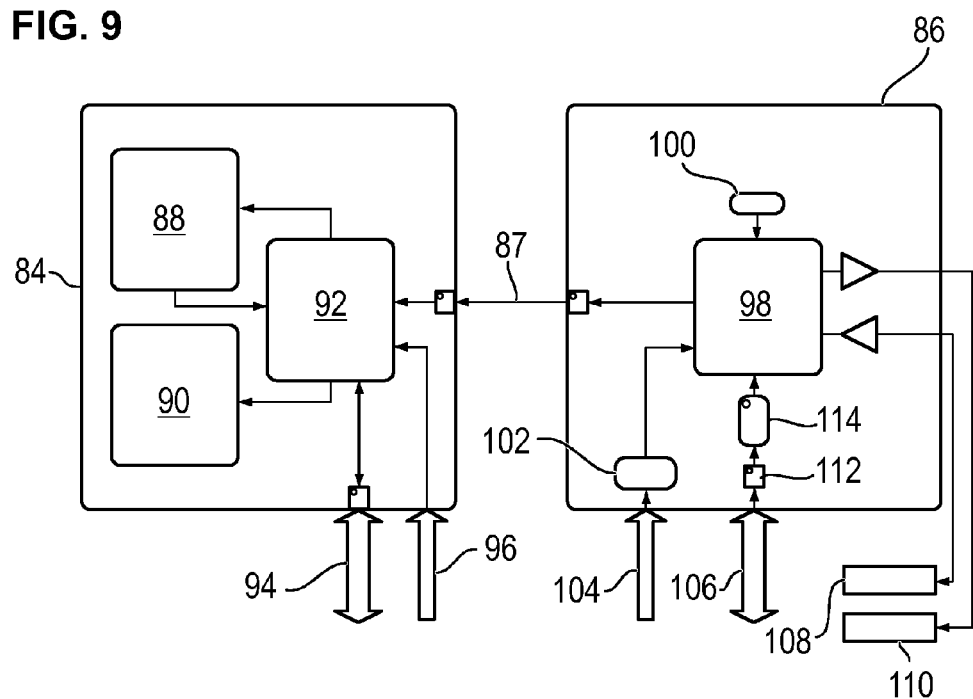
FIG. 9 is a block diagram of the apparatus for sensing the specimen slides.

FIG. 9 is a block diagram from which the operating principles of the apparatus for sensing specimen slides 38 are evident. A camera block 84 is representative of camera 40. A control block 86, which is connected via a connection 87 to camera block 84, is representative of a control system of the apparatus for sensing specimen slides 38. Camera block 84 encompasses an optical system 88, an illumination system 90, and an electronic evaluation system 92. Electronic evaluation system 92 communicates with optical system 88 and illumination system 90. Electronic evaluation system 92 can be read out, controlled, and/or regulated via a USB terminal 94. A first power terminal 96 provides electrical power to camera 40.

Control block 86 encompasses substantially a control unit 98 that communicates with a JTAG interface 100. Control unit 98 is further coupled to a receiver block 108 and a transmitter block 110, which are representative of receiver 68 and transmitter 67, respectively. Control unit 98 is supplied via a second power terminal 104 with electrical power that, for example, can be rectified with the aid of a current transformer 102. Control unit 98 can be controlled with the aid of an external computer via a CAN bus 106, a CAN terminal 112, and a CAN transceiver 114.

Processing and output of the images acquired with camera 40 are handled by electronic evaluation system 92. The latter also takes care of translating the signals of triggering apparatus 67, 68 into suitable control instructions for synchronizing image acquisition with the activation of illumination system 90. The signals of triggering apparatus 67, 68 that are activated by the motion of specimen slides 38 are processed by the switching amplifier that is represented in FIG. 9 by two oppositely directed triangles, and forwarded to control unit 98 and to electronic evaluation system 92. Updating and status querying of a firmware program can occur via JTAG interface 100 or CAN bus 106. The latter eliminates the need for access at the module level, and for additional tools. The firmware of camera 40 preferably emulates an RS232 interface via USB terminal 94. This interface is recognized by a master software program as a serial device, and the images of camera 40 can be read via a standard communication system for serial devices and further processed.

Figure 10:
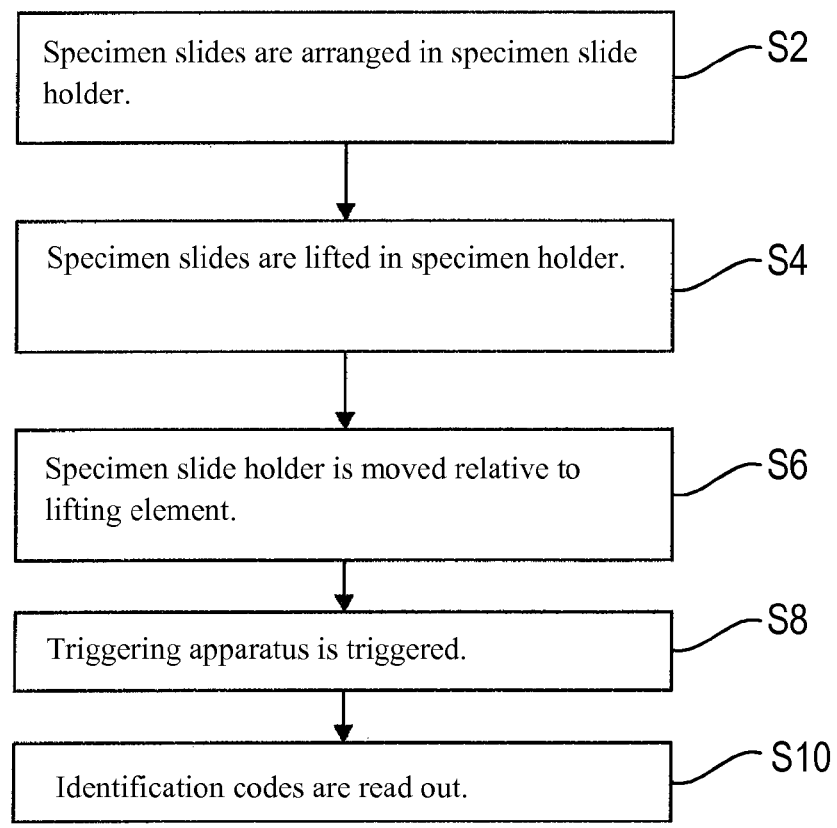
FIG. 10 is a flow chart of a program for sensing the specimen slides.

FIG. 10 shows a flow chart of a program for sensing specimen slides 38, in particular for controlling the apparatus for sensing specimen slides 38. In a step S2, specimen slides 38 are arranged in specimen slide holder 42. In a step S4, specimen slides in specimen slide holder 42 are lifted, for example by placing specimen slide holder 42 onto lifting element 50 or by threading lifting element 50 into specimen slide holder 42 from bottom to top. In a step S6, specimen slide holder 42 is moved relative to lifting element 50 so that specimen slides 38 drop successively at edge 52 from the lifted position on lifting element 50 into their final position in specimen slide holder 42. In a step S8, triggering apparatus 40 is triggered, for example with the aid of triggering apparatus 67, 68 that is activated by specimen slides 38. In a step S10, the identification codes are read out with the aid of reading apparatus 40 in response to a signal of triggering apparatus 67, 68.

Alternatively to the exemplifying embodiment shown in FIGS. 1, 2, and 3, the apparatus for sensing specimen slides 38 can also be arranged outside oven module 34 and/or outside stainer 20. For example, the apparatus for sensing specimen slides 38 can be operated entirely independently of a further apparatus, for example in order to identify specimen slides 38 prior to processing in a deparaffinization unit. As an alternative thereto, the apparatus for sensing specimen slides 38 can be part of the deparaffinization unit. This may be necessary if specimen slides 38 that are not to be deparaffinized are present in specimen slide holder 42. The apparatus for sensing specimen slides 38 can furthermore be part of a coverslipper (not depicted) for coverslipping the samples on specimen slides 38. Sensing of specimen slides 38 can also be carried out for documentation purposes.

The invention is not to be limited to the specific embodiments disclosed, and modifications and other embodiments are intended to be included within the scope of the invention.

LIST OF REFERENCE NUMERALS

20 Stainer
22 Housing
24 Interior space
26 Cover
28 Monitor
30 Reagent container
32 Gripper arm
34 Oven module
36 Carrier bracket
38 Specimen slide
40 Camera
41 Receiving direction
42 Specimen slide holder
44 Drive unit
46 Horizontal guide
48 Identification space
50 Lifting element
52 Edge
54 Coupling element
56 First motion direction
58 Height
60 Lowering direction
61 Lower edges
62 Labeling field
63 Upper edges
64 Second motion direction
65 Surfaces
66 Camera space
67 Transmitter
68 Receiver
69 Rear sides
70 Sensor
72 Sleeve
74 Bearing block
76 Glass window
78 First sealing ring
80 Second sealing ring
84 Camera block
86 Control block
87 Connection
88 Optical system
90 Illumination system
92 Electronic evaluation system
94 USB terminal
96 First power terminal
98 Control unit
100 JTAG interface
102 Current transformer
104 Second power terminal
106 CAN bus
108 Receiver block
110 Transmitter block
112 CAN terminal
114 CAN transceiver
S2-S10 Steps two to ten

What is claimed is:

1. An apparatus for sensing specimen slides (38), comprising:
  a specimen slide holder (42) in which the specimen slides (38) are arranged, the specimen slides (38) each comprising an identification code for identifying the specimen slide (38);
  a lifting element (50) on which the specimen slides (38) are arranged inside the specimen slide holder (42) in a lifted position;
  a reading apparatus (40) for reading out the identification code;
  a gripper arm (32) that moves the specimen slide holder (42) with the specimen slides (38) onto the lifting element (50) in the lifted position, wherein the gripper arm (32) is configured to move so that the specimen slides (38) drop successively from the lifted position on the lifting element (50) into a final position in the specimen slide holder (42), the identification codes being arranged on the specimen slides (38) to be readable on the specimen slide (38) or a subsequent specimen slide (38) by the reading apparatus 40 after a one of the specimen slides (38) drops into the final position; and
  a triggering apparatus (67, 68) that triggers the reading apparatus (40) to read the corresponding identification code.

2. The apparatus according to claim 1, wherein the lifting element (50) comprises an edge (52) at which the specimen slides (38) drop from the lifting element (50), and wherein a spacing between the edge (52) and the reading apparatus (40) is constant.

3. The apparatus according to claim 1, wherein the lifting element (50) includes a rail or a blade.

4. The apparatus according to claim 1, wherein the reading apparatus (40) includes a camera.

5. The apparatus according to claim 1, wherein the triggering apparatus (67, 68) includes a photoelectric barrier.

6. The apparatus according to claim 1, further comprising an apparatus (20) for processing tissue samples, wherein the apparatus (20) is configured to stain and/or coverslip tissue samples arranged on the specimen slides (38).

7. A method for sensing specimen slides (38), comprising:
arranging a plurality of specimen slides (38) inside a specimen slide holder (42), each specimen slide (38) slide including an identification code for identifying the specimen slide (38);
lifting the plurality of specimen slides (38) into a lifted position with the aid of a lifting element (50);
moving the specimen slide holder (42) with the specimen slides (38) relative to the lifting element (50) so that the specimen slides (38) drop successively from the lifted position into a final position in the specimen slide holder (42), wherein as one of the specimen slides (38) drops under the influence of gravity, the identification code of the specimen slide (38) or of the subsequent specimen slide (38) becomes readable for a reading apparatus (40); and
reading the readable identification code using the reading apparatus (40) in response to a signal from a triggering apparatus (67, 68).

8. The method according to claim 7, wherein the specimen slide holder (42) with the specimen slides (38) is moved onto the lifting element (50) so that the lifting element (50) lifts the specimen slides (38) in the specimen slide holder (42) into the lifted position.

9. The method according to claim 7, wherein the lifting element (50) comprises an edge (52) at which the specimen slides (38) drop off the lifting element (50), and wherein a spacing between the edge (52) and the reading apparatus (40) is held constant.

10. The method according to claim 7, wherein the triggering apparatus (67, 68) is triggered before or as the specimen slides (38) drop into the final position, by the corresponding specimen slide (38).

* * * * *